United States Patent
Sherman

Patent Number: 5,971,980
Date of Patent: *Oct. 26, 1999

[54] SYSTEM FOR CONTROLLING THE ENERGY DELIVERED TO A PATIENT FOR ABLATION

[75] Inventor: Marshall L. Sherman, Cardiff, Calif.

[73] Assignee: Heart Rhythm Technologies, Inc., Temecula, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/899,084

[22] Filed: Jul. 23, 1997

Related U.S. Application Data

[63] Continuation of application No. 08/433,292, May 2, 1995, abandoned.

[51] Int. Cl.⁶ .................................................. A61B 17/39
[52] U.S. Cl. ............................... 606/34; 606/41; 606/42; 607/101
[58] Field of Search .......................... 606/32–34, 37–42, 606/45–50; 607/100–102, 122

[56] References Cited

U.S. PATENT DOCUMENTS

| | | | |
|---|---|---|---|
| 4,281,373 | 7/1981 | Mabille | 606/38 |
| 4,559,943 | 12/1985 | Bowers | 606/37 |
| 4,739,759 | 4/1988 | Rexroth et al. | 606/37 |
| 4,907,589 | 3/1990 | Cosman | 606/41 |
| 4,936,281 | 6/1990 | Stasz | 606/48 |
| 5,300,068 | 4/1994 | Rosar et al. | 606/32 |
| 5,383,874 | 1/1995 | Jackson et al. | 606/1 |
| 5,385,146 | 1/1995 | Goldreyer | 128/642 |
| 5,405,346 | 4/1995 | Grundy et al. | 606/41 |
| 5,423,808 | 6/1995 | Edwards et al. | 606/34 |
| 5,433,198 | 7/1995 | Desai | 128/642 |
| 5,437,664 | 8/1995 | Cohen et al. | 606/34 |
| 5,438,302 | 8/1995 | Goble | 331/167 |
| 5,447,509 | 9/1995 | Mills et al. | 606/1 |
| 5,447,529 | 9/1995 | Marchlinski et al. | 607/99 |
| 5,496,312 | 3/1996 | Klicek | 606/34 |
| 5,514,130 | 5/1996 | Baker | 606/41 |
| 5,540,681 | 7/1996 | Strul et al. | 606/34 |
| 5,769,847 | 6/1998 | Panescu et al. | 606/42 |
| 5,810,802 | 9/1998 | Panescu et al. | 606/31 |

FOREIGN PATENT DOCUMENTS

94/24949  11/1994  WIPO ................................ 606/34

*Primary Examiner*—Michael Peffley
*Attorney, Agent, or Firm*—Fulwider Patton Lee & Utecht, LLP

[57] ABSTRACT

A power control system and method controls a power generator to vary the duty cycle of a power output provided to a delivery instrument for delivering that power to a site in a patient for ablation. The peak power can be raised and the duty cycle lowered to result in deeper lesions. However, the effective power is controlled so that it does not exceed a predetermined level. A power output having a higher peak power for producing deeper lesions can be obtained by using a lower duty cycle having a longer "off" period in order to deliver more power to the ablation site without overheating the delivery instrument. The maximum peak power that may be selected is determined in accordance with the structural limitations of the delivery instrument. The temperature of the delivery instrument is monitored, and the duty cycle is lowered when the temperature exceeds a predetermined maximum limit. After the instrument has cooled sufficiently, the duty cycle is then increased to its previous level.

29 Claims, 6 Drawing Sheets

SYSTEM FOR CONTROLLING THE ENERGY DELIVERED TO A PATIENT FOR ABLATION

This application is a continuation of application Ser. No. 08/433,292, filed on May 2, 1995 (now abandoned).

BACKGROUND

The invention generally relates to power control, and more particularly, to controlling the energy delivered to a patient for more effective energy transfer.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of or damage to the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as cardiac arrhythmia.

Electrophysiological ablation is a procedure often successful in terminating cardiac arrhythmia. This procedure involves applying sufficient energy to the interfering tissue to ablate that tissue thus removing the irregular signal pathway. However, before the ablation procedure can be carried out, the interfering tissue must first be located.

One location technique involves an electrophysiological mapping procedure whereby the electrical signals emanating from the conductive endocardial tissues are systematically monitored and a map is created of those signals. By analyzing that map, the interfering electrical pathway can be identified. A conventional method for mapping the electrical signals from conductive heart tissue is to percutaneously introduce an electrophysiology ("EP") catheter having mapping electrodes mounted on its distal extremity. The catheter is maneuvered to place those electrodes in contact with or in close proximity to the endocardium of the patient's heart. By monitoring the electrical signals at the endocardium, aberrant conductive tissue sites responsible for the arrhythmia can be pinpointed.

Once the origination point for the arrhythmia has been located in the tissue, the physician may use an ablation procedure to destroy the tissue causing the arrhythmia in an attempt to remove the electrical signal irregularities and restore normal heart beat or at least an improved heart beat. Successful ablation of the conductive tissue at the arrhythmia initiation site usually terminates the arrhythmia or at least moderates the heart rhythm to acceptable levels.

The distal end of an EP catheter may include mapping electrodes as well as an ablation device for performing the ablation procedure. One type of ablation device includes an ablation electrode that emits radio frequency ("RF") energy to heat the target tissue to a temperature high enough to cause ablation of that tissue. Another type of ablation devices comprises an ultrasonic device, such as a piezoelectric device.

As the ablation procedure progresses, heat is generated and the surrounding blood is exposed to this heat. At approximately 100° C., charring and boiling of the blood take place. Coagulation may also occur. Charring is particularly troublesome at the surface of the ablation device because emboli may form on the surface of the device to an extent that the catheter must be removed and cleaned before the procedure can continue. Furthermore, charring and coagulation can cause a substantial increase in the impedance and a corresponding decrease in the power delivery to the tissue. Too great a rise in impedance can result in sparking and thrombus formation within the heart, both of which are undesirable.

Because part of the ablation transducer is in contact with the blood in the heart, blood boiling, emboli development, and clotting can result if the surface temperature of the transducer exceeds 90–100° C. If this occurs, the ablation procedure must be stopped regardless of whether the entire ablation procedure has been completed. The catheter must then be removed from the patient, the attached necrotic tissue removed, and the catheter reinserted into the patient. Such cleaning processes require extra time and unduly prolong the ablation procedure. To avoid such undesirable circumstances, a temperature sensor may be incorporated at the distal end of the catheter to monitor and maintain a selected temperature during ablation. The ablation process can then be controlled so that the temperature is not allowed to increase above a predetermined level.

In many cases, the target tissue extends relatively deeply in the endocardium. To successfully ablate that tissue, deeper lesions are necessary. However, merely increasing the power applied to the ablation device does not necessarily result in a lesion of greater depth. Power at too high a level can damage the delivery instrument, or cause charring and boiling of the surrounding blood and tissues, thereby necessitating termination of the application of energy and prematurely shortening the ablation procedure before the lesion can be developed to the desired depth.

Hence, those skilled in the art have recognized the need to improve the delivery of energy to the patient. Improved delivery of ablation energy is needed to produce deeper lesions in the heart tissue while at the same time, controlling the temperature developed at the site. The present invention fulfills these needs and others.

SUMMARY OF THE INVENTION

Briefly and in general terms, the present invention is directed to a power control system for delivering energy to a biological site. A power control system comprises a power generator for generating a power output having a controllably variable peak power, a power delivery device connected to the power generator, the power delivery device adapted to deliver energy to the biological site in response to the power output of the power generator, a processor for controlling the power generator to generate the power output within a series of sequential time periods in which the peak power remains constant within each time period, and the peak power in one sequential time period varies from the peak power in the next sequential time period, and wherein the processor further varies the length of each time period in accordance with the peak power of that time period. The power delivery device can be mounted on a catheter for delivering energy to the biological site for ablation.

In another aspect, the series of sequential time periods is characterized by the repetition of an on period followed by an off period, wherein the peak power during the on period is greater than zero, and the peak power during the off period is substantially equal to zero. The ratio of the on periods to the total time duration, which is the sum of the on and off periods of the series of sequential time periods, represents the duty cycle of the power output generated by the power generator.

In a further aspect of the invention, the duty cycle is varied while the peak power is set to a high level so as to produce deeper lesions during ablation without generating excessive heat from the power delivery device element which may char and boil the surrounding blood and tissues. While the duty cycle is being varied, the peak power is kept constant during ablation. The values of the peak power and the duty cycle are selected so that the power output does not exceed a predetermined effective power level.

In yet another aspect, the power control system further includes a temperature sensor for sensing the temperature at the power delivery device, and producing a temperature signal representing the sensed temperature. The processor receives the temperature signal and increases the duty cycle when the temperature signal represents a temperature below a threshold temperature. The duty cycle is decreased when the temperature signal represents a temperature above a threshold temperature.

In another aspect of the invention, the peak power of a period is kept constant while the duty cycle is varied in accordance with the temperature at the power delivery device.

Other features and advantages of the invention will become apparent from the following detailed description taken in conjunction with the accompanying drawings, which illustrate by way of example, the features and advantages of the invention.

DETAILED DESCRIPTION OF THE PREFERRED EMBODIMENTS

Figure 1:
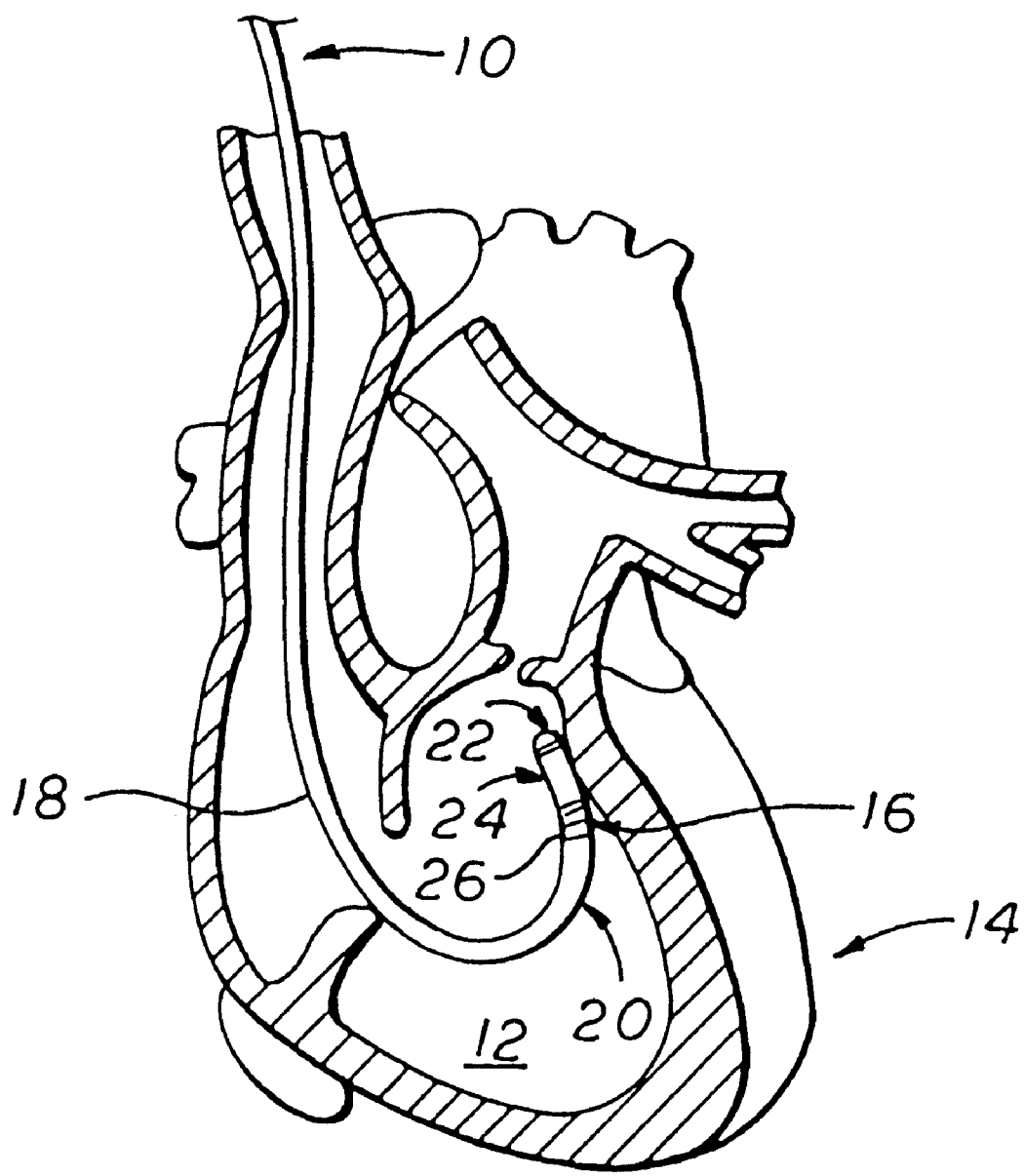
FIG. 1 is a diagrammatic view of a human heart in partial section showing an electrophysiological catheter disposed internally and located so that one side of a "side-fire" energy transducer mounted at its distal end is against the endocardium for performing an electrophysiological procedure.

In the following description, like reference numerals will be used to refer to like or corresponding elements in the different figures of the drawings. The following discussion will be based on the example of the catheter 10 being percutaneously inserted into a patient in order to perform an ablation procedure. As shown in FIG. 1, an electrophysiology ("EP") type catheter 10 can be inserted percutaneously into a patient and steered into the right ventricle 12 of a human heart 14 for localized diagnosis or treatment of the endocardial tissue 16 thereof. The catheter includes, in this case, an elongated catheter body 18 having a distal end 20 with an electrode 22 mounted at the distal tip, a power delivery device 24, in this case a cylindrical ultrasonic transducer, mounted proximal to the tip electrode 22, and a band electrode 26 mounted proximal to the power delivery device 24. The electrodes 22 and 26 and the transducer 24 may be individually or simultaneously actuated to perform various electrophysiological procedures. In FIG. 1, the distal end of the catheter is shown parallel to and in contact with the endocardium for performing a side-fire EP ablation procedure with the transducer 24. As used herein, a "side-fire" device is one that is mounted such that it conducts energy sideways in relation to the catheter shaft. An "end-fire" device is one that is mounted such that it conducts energy in the direction of the longitudinal axis from the distal tip of the catheter shaft.

The distal end 20 of the elongated catheter body 18 is steerable and has sufficient torsional and axial rigidity for maneuvering the distal end to selected sites within the heart chamber. The catheter body 18 is of sufficient length to allow for a transluminal percutaneous brachial approach to the heart of an adult patient or a transluminal percutaneous femoral approach, for example.

Figure 2:
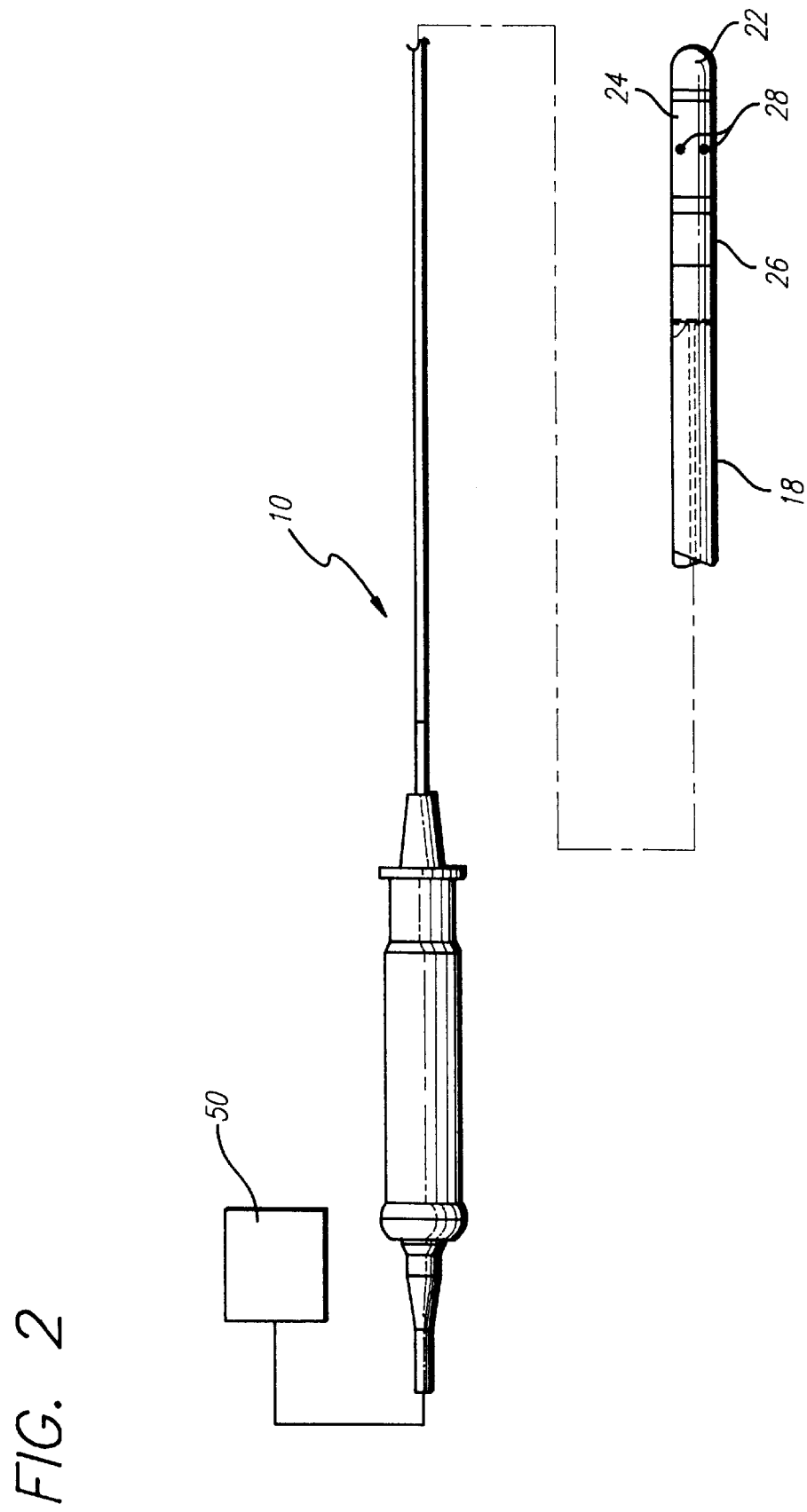
FIG. 2 is a partial elevation view of an electrophysiological catheter showing an energy delivery device at the distal end and a connector at the proximal end for electrical connection.

Referring now in more detail to FIG. 2, the distal tip electrode 22 may be a mapping-type electrode used to receive electrical signals from adjacent endocardial tissue for locating aberrant conductive tissues. Suitable materials for the tip electrode 22 include pure platinum, a platinum iridium alloy such as "platinum 10 iridium" (90% platinum 10% iridium), a gold alloy, pure titanium, and/or pure tungsten. The band electrode 26, proximal to the transducer 24, may also be used either individually or simultaneously with the tip electrode 22 to perform EP mapping procedures. A plurality of temperature sensors 28 (in this case three) are located in the transducer 24. More or fewer of each of these electrodes, sensors or transducers may be used depending upon the particular application or requirements of the electrophysiological procedure involved.

The temperature sensors 28 are preferably thermocouples having elongated leads for sending temperature signals to the proximal end of the catheter. The temperature sensors 28 should be mounted so as to provide an accurate temperature at the distal end of the catheter. Where the ablation transducer 24 is a piezoelectric device for emitting ultrasound energy, the vibration of the transducer generally makes mounting a temperature sensor directly on the transducer itself difficult. However, applicant references the copending U.S. patent application Ser. No. 08/434,004, entitled "CATHETER HAVING ULTRASONIC DEVICE" by Thomas Castellano, now U.S. Pat. No. 5,606,974 filed on the same day as the present application, which discloses a temperature sensor mounted in a piezoelectric transducer for ablation, and hereby incorporates by reference that application in the present application. The peak temperature signals from the plurality of temperature sensors can inform the physician of the temperature sensed.

The side-fire transducer 24 is mounted adjacent the distal tip of the catheter 10. In this embodiment, the transducer 24 is a piezoelectric transducer having a generally cylindrical shape. The cylindrical piezoelectric transducer 24 directs ultrasonic acoustic energy in a radial outward direction for side-fire operation. U.S. patent application Ser. No. 08/434, 004, entitled "CATHETER HAVING ULTRASONIC DEVICE" by Thomas Castellano, now U.S. Pat. No. 5,606, 974, filed on the same day as the present application, discloses a suitable side-fire transducer for ablation, and which has been incorporated by reference in the present application. However, the transducer 24 may take other forms. Other types of energy may be used for ablation as may other types of transducers or energy delivering devices.

During the ablation procedure, the target tissue is heated. Because of its mass, it has a greater thermal inertia than the transducer itself. Thus, when power is discontinued to the transducer, its temperature will decrease faster than the temperature of the target tissue. Additionally, at least a part of the transducer is located in the cooler flowing blood that will carry away some of the heat of the transducer. Thus the power supply to the transducer can be shut off, the transducer can be allowed to cool, and the power can be resumed to the transducer before the temperature of the target tissue decreases to any substantial degree. These steps can be accomplished by controlling the duty cycle of the power generator supplying ablation power to the transducer.

Because the transducer is allowed to cool during the portion of the duty cycle where no power is being applied, it has been found that higher peak power can be applied. It has also been found that applying a higher peak power can result in deeper lesions if the duty cycle control discussed above is followed. For example, in tissue having a resistance of approximately one-hundred ohms, a voltage of fifty volts with a one-hundred percent duty cycle will result in an effective power level of twenty-five watts. For a signal having a voltage twice the previous example, i.e., one-hundred volts, with a twenty-five percent duty cycle, the effective power or heating value of the ablation signal would also be twenty-five watts; however, a higher voltage was used. The effective power or "rms power value" is the peak power times the duty cycle. The rms power value indicates the effective power being generated and applied to the ablation site.

Thus the effective power level delivered to the target ablation tissue can be kept the same as in prior techniques to avoid charring, coagulation and other undesirable effects, while the peak power being applied to the tissue can be raised substantially, resulting in deeper lesions. Control over the duty cycle also permits control over the temperature so that charring and blood boiling can be avoided. Thus, the duty cycle may be varied in accordance with two separate criteria. First, after the peak power is set, the duty cycle is then selected to maintain a certain effective power for the ablation output or maintain the power output below a predetermined maximum power. Second, the duty cycle can be varied for temperature control. One or both of these control criteria may be used in determining the duty cycle of the ablation energy output.

To maintain a selected temperature at the distal end of the catheter, the signal from the temperature sensor 28 is monitored. If the temperature signal is rising above a predetermined temperature, for example 85° C., the duty cycle of the power output is lowered result in a longer "off" period for the transducer, thereby allowing the transducer to cool down. If the temperature signal is decreasing below a predetermined temperature, the duty cycle is then increased to a higher level to apply more effective power to the ablation site. During this time, the peak power applied to the transducer 24 in one embodiment is kept constant. Preferably a "steady state" control system is used to control the duty cycle so as to maintain the temperature at a selected temperature.

Figure 3:
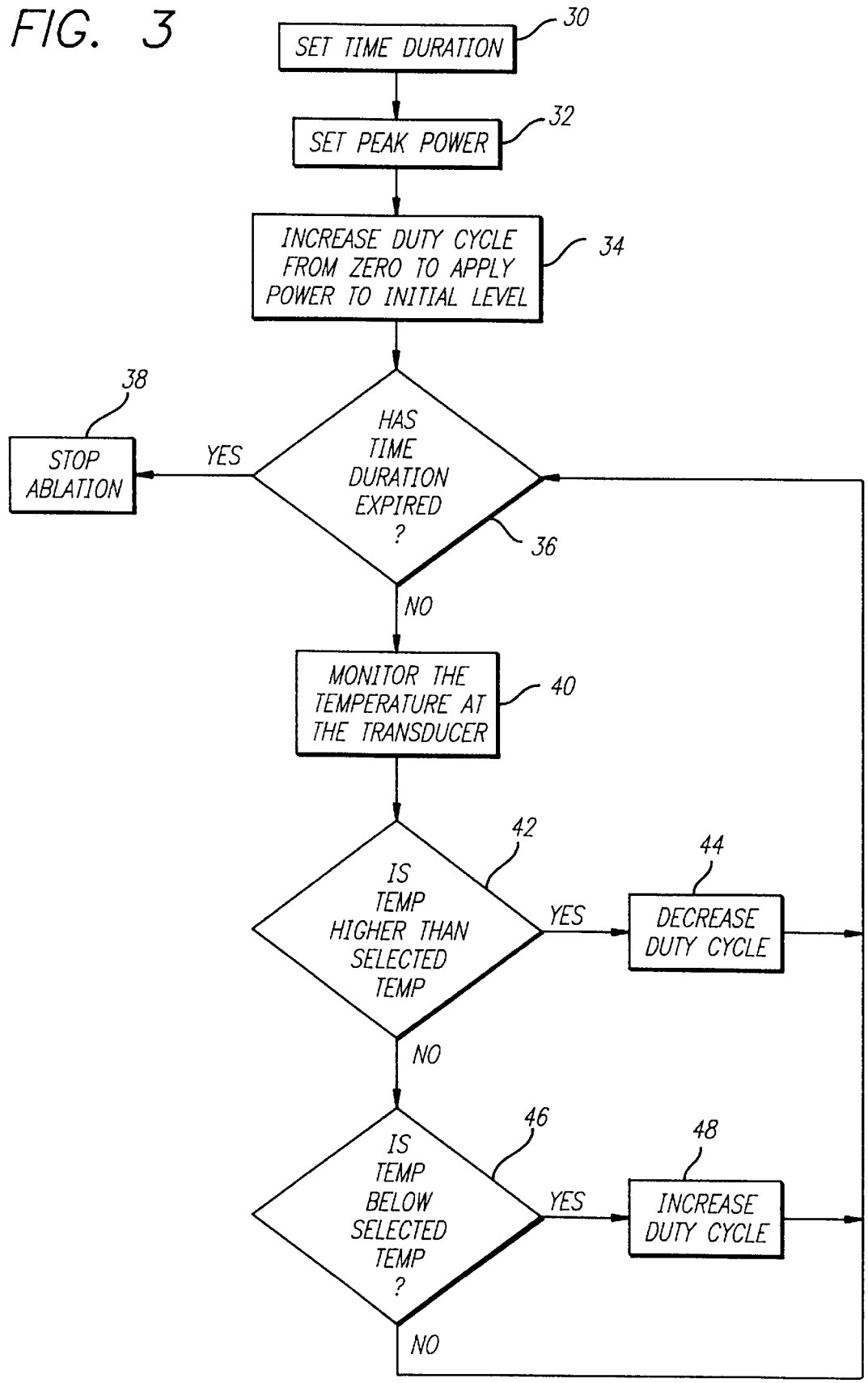
FIG. 3 is a flow chart illustrating the steps for controlling the duty cycle in accordance with the present invention.

FIG. 3 is a flow chart illustrating the operation of a power control system for an ablation generator in accordance with aspects of the present invention. The time duration for the application of ablation energy is set 30, preferably by the operator of the system. The peak power to be generated by the system is also set 32. The processor then sets 34 the duty cycle of the power generator to a value greater than zero but less than one-hundred percent. In setting the duty cycle, the processor considers the peak power selected so as not to exceed a predetermined effective power level, such as twenty-five watts. For example, the processor may slowly increase the duty cycle from zero to twenty percent to arrive at this effective power level in accordance with the selected peak power for the power output. During the ablation procedure, the passage of time is monitored 36 and the procedure stops 38 when the selected time duration expires.

During the procedure in the embodiment shown in FIG. 3, a temperature sensor is used to sense the temperature at the distal end of the catheter and the sensed temperature is monitored 40 to control the duty cycle. When the temperature is too high, the duty cycle is decreased 44 to allow the transducer to cool. If the temperature is too low 46, the duty cycle is increased 48 to apply more power.

In one embodiment, a steady state control system is used to maintain a predetermined temperature. The system employs a P.I.D. ("proportional-integral-derivative") control loop well known to those skilled in the art to regulate the duty cycle in order to maintain the monitored temperature at a selected steady state level. The corrective P.I.D. adjustment of the duty cycle is proportional to the linear combination of the error, the integral of the error, and the derivative of the error. In this instance, the error represents the difference between the monitored temperature and the desired steady state temperature.

Figure 4:
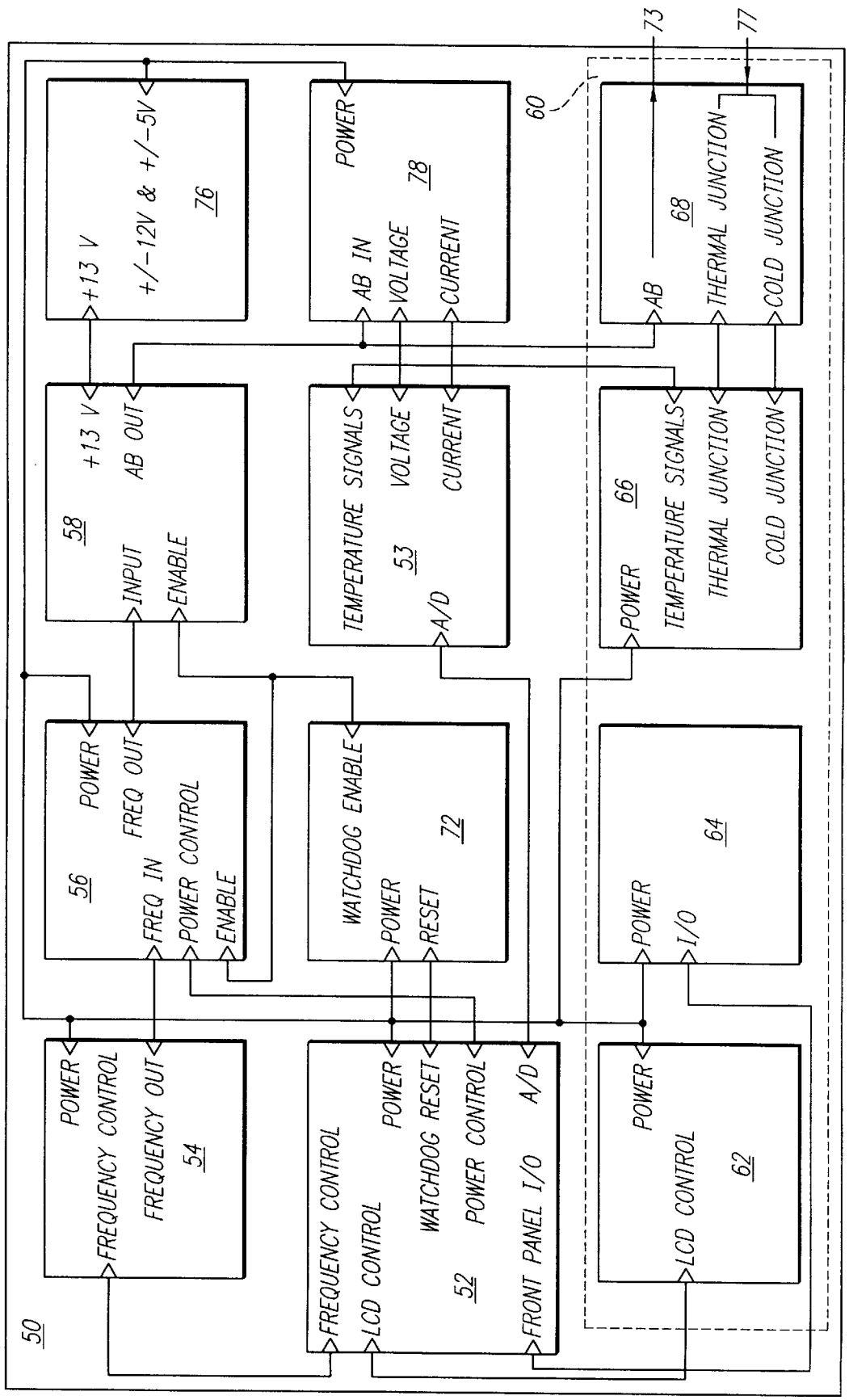
FIG. 4 is a block diagram illustrating the power control system for controlling the duty cycle of an ablation device in accordance with principles of the present invention.

Referring now to FIG. 4, a block diagram of an embodiment of an ablation generator 50 is presented. The output line 73 carries the power output from the power amplifier 58 to the transducer 24 at the distal end of the catheter to provide the energy needed for ablation (FIG. 2). The input line 77 carries temperature sensor signals from the temperature sensors located at the distal end of the catheter. These temperature sensor signals are processed in the temperature sensor processor 66 which outputs a temperature signal representing the temperature sensed to the control processor 52 through an analog-to-digital ("A/D") converter 53. For example, the temperature sensor processor 66 can select the highest peak temperature signal from the temperature sensors (peak temperature) and provide only that peak value to the control processor 52.

The control processor 52 also controls the LCD display 62 of the front panel 60. The LCD display 62 indicates the operating parameters of the ablation procedure such as the selected time duration. The ablation generator 50 further includes a watchdog circuit 72 for disabling the power control 56 and the power amplifier 58 in the event of an error or fault condition. The power control 56 and the power amplifier 58 are enabled by the watchdog circuit 72 in accordance with condition and reset signals from the control processor 52.

The ablation generator 50 preferably generates a power output having a sine wave. The frequency synthesizer 54 controls the frequency of the power output from the ablation generator 50. The control processor 52 controls the frequency synthesizer 54 and further controls the operation of the power control 56. The output of the power control 56 is sent to the power amplifier 58 in order to produce the power output for ablation through the catheter connector 68 and to control the duty cycle. The power amplifier 58 is responsive to the output of the power controller 56 which is controlled by the processor 52 via the "power control" connection. The ablation generator 50 produces a power output having a peak power and duty cycle from the power amplifier 58. The peak power and duty cycle of the ablation operator 50, and thus the effective power, are variably controlled by the control processor 52 through the "power control" connection.

The power supply 76 provides power to the various elements of the ablation generator 50. A voltage and current monitor 78 monitors the voltage and current of the ablation energy and provides signals representing these values through the A/D converter 53 to the control processor 52. The monitored voltage and current are used by the processor to calculate data values, such as the peak power, impedance and effective power, which in turn are used to control the proper duty cycle for the ablation procedure. Too great a rise in the impedance may indicate that charring of the tissue has begun, in which case the control processor will lower the duty cycle of the power output from the ablation generator. In a case where the impedance increases to a predetermined threshold, such as twenty-five percent above the initial impedance, the ablation power would be interrupted and the ablation procedure stopped as tissue charring, coagulation, or other energy transfer obstacles have occurred. The impedance change is monitored in percentage units in one embodiment, and the relative impedance rise is considered.

As used herein, the "duty cycle" is the ratio of the time during which power is applied to the target tissue over the total time duration of the treatment (i.e., the sum of the on-load and off-load periods), expressed as a percentage. For a power output having a duty cycle of 25% applied over a time duration of sixty seconds, the total on-load period during which power is actually being applied to the patient would be fifteen seconds.

Switches 64 are provided on the front panel 60 to control operational parameters of the ablation procedure. The control processor 52 controls the duty cycle so that the power output of the ablation generator 50 which does not exceed a predetermined maximum power level. This maximum power level may be limited by the structural characteristics of the power delivery device, by the power level known to cause charring, or other considerations. Preferably the peak power is maintained at a constant value while the duty cycle is varied to attain the predetermined effective power level. The processor 52 controls the duty cycle to be less than 100%, and is preferably maintained below 50% in order to allow for a higher peak power. As the duty cycle is decreased below 100%, the peak power can be increased to generate a power output having an effective power at or below the predetermined maximum power level for ablation such as twenty-five to thirty watts. In the case where a temperature sensor is disposed at the ablation device, the control processor will further consider the temperature signal in controlling the duty cycle as described above. However, the processor 52 will not allow the duty cycle to increase to a level where the effective power exceeds the predetermined maximum effective power level. In one case where a piezoelectric device is used, the predetermined maximum power level is set at thirty watts to avoid fracturing the device.

Figure 5:
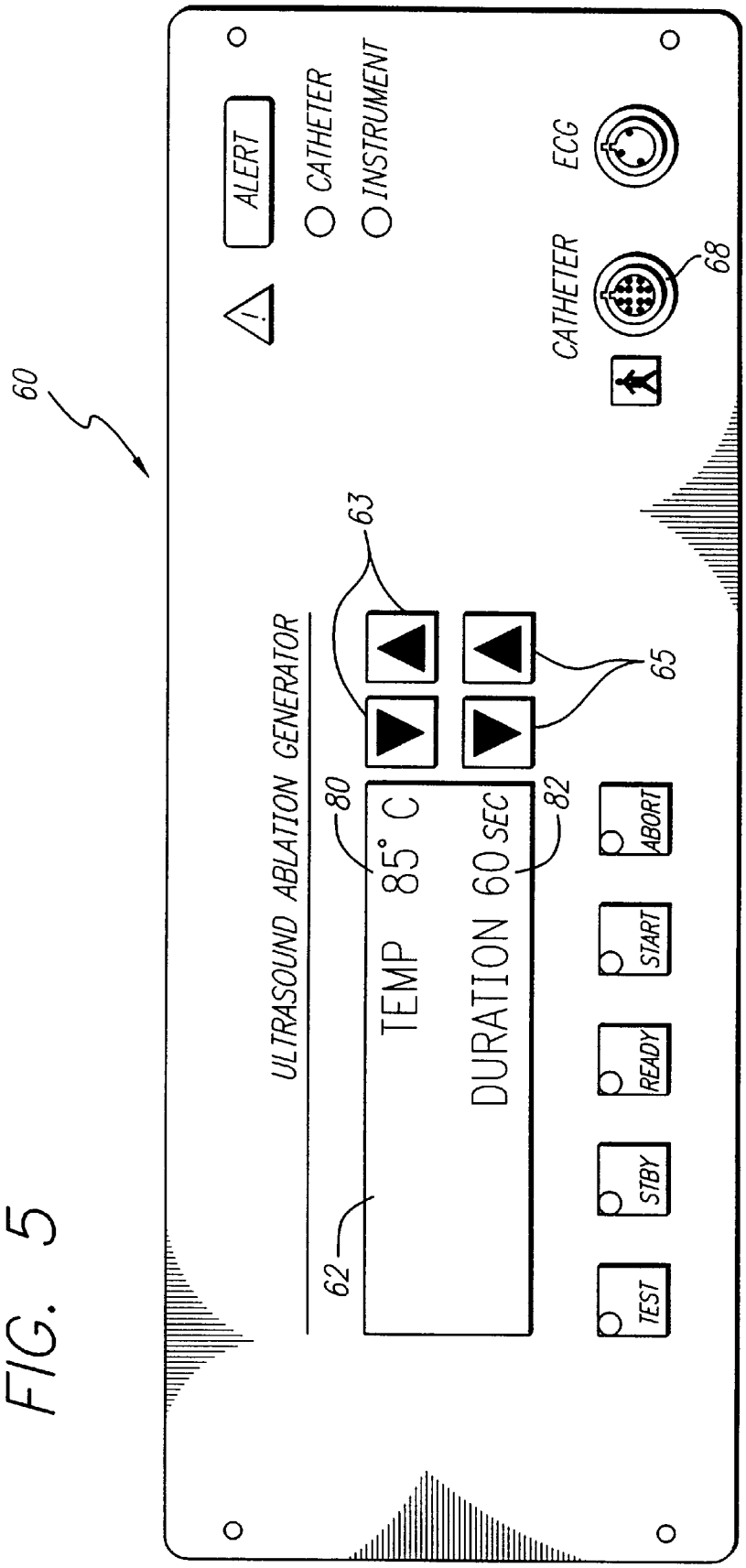
FIG. 5 is an elevational view of the front display panel of a power control system usable to control the duty cycle of ablation energy applied to the ultrasonic ablation device of FIG. 1.

FIG. 5 presents one embodiment of the front display panel 60 (FIG. 4) of an ultrasound ablation generator in accordance with aspects of the present invention. Switches 63 are provided for setting the desired steady state temperature, and other switches are provided for setting the time duration for the ablation procedure. The LCD display 62 indicates both the selected set point temperature 80 and the selected duration 82. The above description of the display and the switches of the front display panel are illustrative only, and other values can be displayed in accordance with the particular application or procedure involved. In one ultrasound ablation embodiment, the peak power is not user controllable because a temperature sensing system is provided. The peak power is held constant and the duty cycle is varied automatically in accordance with the temperature feedback system.

Figure 6:
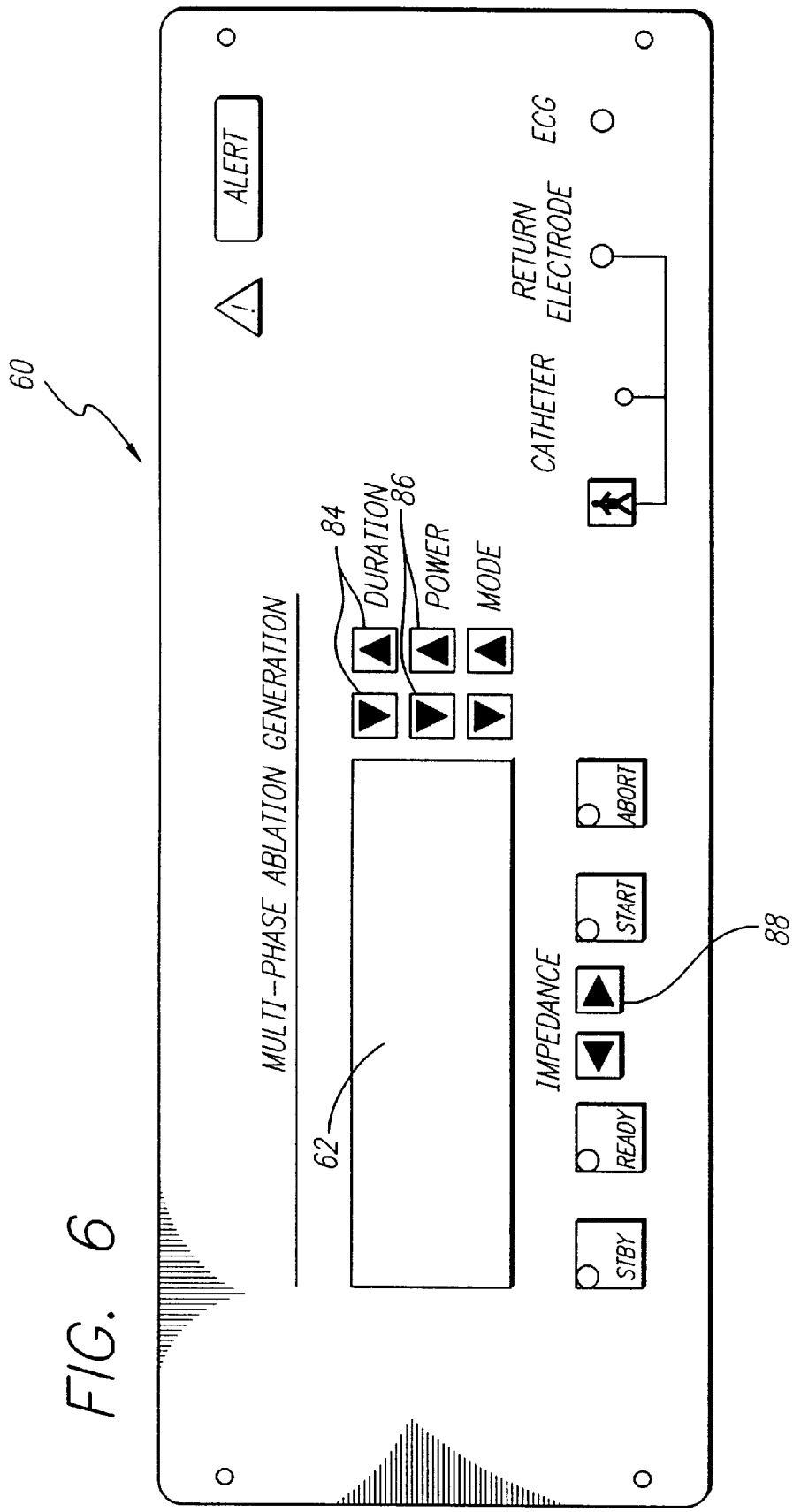
FIG. 6 is an elevational view of the front display panel of a power control system usable to control the duty cycle of energy to be applied to an RF electrode or electrodes for ablation.

FIG. 6 presents another embodiment of the front display panel, in this case, that of a multi-phase RF ablation generator in accordance with aspects of the present invention. No temperature feedback system is provided in this embodiment. The LCD display 62 indicates the selected duration and the selected peak power. The duration and peak power may be selectively increased or decreased by the activation of front panel switches 84 and 86 respectively. The LCD display 62 provides data concerning the ablation procedure. The effective power is preferably maintained within a range of twenty-five to thirty watts. In one embodiment of an RF system, the peak power available from the front panel switches 86 can be set as high as ninety watts. The processor controls the duty cycle to maintain the delivery of an effective power level below the predetermined effective power. Additionally, the impedance is monitored as the duty cycle may be further controlled in accordance with the impedance to avoid extreme impedance rises (for example, twenty-five percent) resulting from the application of excessive power. In the case of FIG. 6, a front panel impedance switch 88 permits the user to select the percentage rise in impedance at which point the processor automatically discontinues the application of ablation energy.

The following is an example of the advantageous results that have been obtained by using aspects of the invention. An ablation generator was then set to produce an output of 30 watts with a 100% duty cycle for 60 seconds. This ablation energy was applied to target tissue having a temperature of 37° C. (98.6° F.). A lesion having a depth of 4 millimeters (mm) was obtained at this ablation setting. An ablation generator was then set to produce an output at 500 KHz with a peak power of 90 watts and a 33⅓% duty cycle over a time period of 60 seconds. This second ablation procedure performed in accordance with the duty cycle power control method resulted in a lesion having a depth of 8 mm. Thus even though both procedures delivered an effective power level of thirty watts, the procedure using a high peak power and variable duty cycle control resulted in a lesion twice as deep.

While the invention has been described herein in terms of certain embodiments, those skilled in the art will recognize that various modifications and improvements can be made to the invention without departing from the spirit and scope of the invention. Accordingly, it is not intended that the invention be limited, except as by the appended claims.

What is claimed is:

1. An apparatus for delivering energy to biological tissue for a predetermined time duration for ablation, said apparatus comprising:

a power source for producing a power output having alternating instances of high peak power and very low power, said power output having variable power levels and a variable duty cycle for controlling the duration of said high peak power and very low power instances, said power source responsive to control signals for setting said power level and duty cycle of said power output;

a power delivery device connected to said power source, said power delivery device adapted to deliver energy to the tissue in response to said power output; and a processor for providing said control signals to said power source, said control signals for:

setting said high peak power level high and said duty cycle low, relative said high peak power level, so that the cumulative instances of high peak power occurring during said predetermined time duration is sufficient to introduce a lesion in the ablation tissue while the effective power is maintained at a level lower than a predetermined threshold effective power level which would produce either charring or coagulation of the ablation tissue or arcing at said power delivery device; and setting said duty cycle so that the effective power does not exceed said predetermined threshold effective power;

wherein said control signals control the depth of said lesion by varying said high peak power level while varying said duty cycle to maintain said effective power below said predetermined threshold effective power.

2. The apparatus of claim 1 wherein said control signals increase said high peak power to increase the depth of said lesion while reducing said duty cycle to maintain said effective power below said threshold effective power.

3. The apparatus of claim 1 wherein said control signals maintain said effective power between approximately 25 watts and approximately 30 watts.

4. The apparatus of claim 1 wherein said control signals maintain said duty cycle below approximately 50 percent.

5. The apparatus of claim 1 wherein said control signals set said high peak power to approximately 90 watts, said predetermined time duration to approximately 60 seconds and said duty cycle to approximately 33.3%.

6. The apparatus of claim 1 further comprising:

an impedance monitor that monitors the impedance of the biological tissue as energy is being delivered by said power delivery device and provides an impedance signal representative of the impedance to said processor;

wherein said processor compares said impedance signal to a predetermined threshold impedance stored in said processor and, if said impedance signal exceeds said threshold impedance, adjusts said control signals to reduce said duty cycle.

7. The apparatus of claim 6 wherein said impedance monitor senses the voltage and the current of the power applied to said power delivery device and said processor compares the voltage and current to determine the impedance at the biological tissue.

8. The apparatus of claim 6 wherein said predetermined threshold impedance is the impedance of the biological tissue at which tissue charring or coagulation occurs.

9. The apparatus of claim 6 wherein said predetermined threshold impedance is approximately 25% above the impedance of the biological tissue prior to the delivery of energy.

10. The apparatus of claim 1 further comprising:

a temperature sensor for sensing the temperature at said power delivery device, said temperature sensor providing a temperature signal representative of the sensed temperature to said processor;

wherein said processor compares said temperature signal to a predetermined first threshold temperature stored in said processor and, if said temperature signal represents a temperature above said predetermined first threshold temperature, adjusts said control signal to reduce said duty cycle.

11. The apparatus of claim 10 wherein said processor compares said temperature signal to a predetermined second threshold temperature stored in said processor and, if said temperature signal represents a temperature below said predetermined second threshold temperature, adjusts said control signals to increase said duty cycle.

12. An apparatus for delivering energy to cardiac tissue for a predetermined time duration for ablation, the apparatus comprising:

a power source for producing a power output having alternating instances of high peak power and very low power, said power output having variable power levels and a variable duty cycle for controlling the duration of said high peak power and very low power instances, said power source responsive to control signals for setting the power level and duty cycle of the power output;

a catheter having a proximal end and a distal end;

an electrode operably connected to said power source and mounted at said distal end of the catheter, said electrode producing an energy output in response to said power output; and a processor connected to said power generator, said processor for providing said control signals to said power source, said control signals for:

setting said high peak power level high and said duty cycle low, relative said high peak level, so that the cumulative instances of high peak power occurring during said predetermined time duration is sufficient to introduce a lesion in the ablation tissue while the effective power is maintained at a level below a predetermined threshold effective power level which would produce either charring or coagulation of the ablation tissue or arcing at the electrode; and controlling the depth of said lesion by varying said high peak power level while varying said duty cycle to maintain said effective power below said predetermined threshold effective power.

13. The apparatus of claim 12 wherein said control signals increase said high peak power to increase the depth of said lesion while reducing said duty cycle to maintain said effective power at or below said threshold effective power.

14. The apparatus of claim 12 further comprising:

a temperature sensor mounted to said catheter for sensing the temperature at said electrode, said temperature sensor providing a temperature signal representative of said sensed temperature; and an impedance monitor that monitors the impedance of the cardiac tissue as energy is being delivered by said electrode and provides an impedance signal representative of the impedance;

wherein said processor is connected to said temperature sensor and said impedance monitor and is adapted to receive said temperature signal and said impedance signal, said processor responsive to said temperature signal to adjust said control signals to reduce said duty cycle when the temperature represents a temperature above a predetermined first threshold temperature stored in said processor, said processor also responsive to said impedance signal to adjust said control signals to reduce said duty cycle when said impedance signal represents an impedance above a predetermined threshold impedance stored in said processor.

15. The apparatus of claim 14 wherein said processor is further responsive to said temperature signal to adjust said control signals to increase said duty cycle when said temperature signal represents a temperature below a second threshold temperature stored in said processor.

16. The apparatus of claim 14 wherein said control signals maintain said high peak power constant while varying said duty cycle in accordance with the temperature at said electrode.

17. The apparatus of claim 16 wherein said control signals maintain said high peak power constant while varying said duty cycle so that the effective power does not exceed said predetermined threshold effective power level.

18. The apparatus of claim 14 further comprising a second temperature sensor mounted to said catheter for sensing the temperature at said electrode at a location removed from said first temperature sensor, said second temperature sensor producing a second temperature signal representing the sensed temperature.

19. The apparatus of claim 18 wherein the processor is responsive to said second temperature signal for comparing said first temperature signal with said second temperature signal to determine which of the compared signals is greater, said processor responsive to the greater of the compared signals to adjust said control signals to lower said duty cycle when the greater of the compared signals is above said predetermined threshold temperature.

20. A method of applying energy to cardiac tissue for ablation using an electrode connected to a power source, said power source producing a power output having alternating instances of high peak power and very low power, said power output having variable power levels and a variable duty cycle for controlling the duration of high peak power and very low power instances, said power source also having a timer for allowing the application of energy to the cardiac tissue for a set time duration, said method comprising the steps of:

placing said electrode at the cardiac tissue;

setting said time duration for the ablation procedure;

setting said high peak power level high; and setting the duty cycle of said power output low, relative said high peak power level, so that the cumulative instances of high peak power occurring during said set time duration is sufficient to introduce lesions in the tissue while the effective power during said set time duration is maintained at a level lower than a threshold effective power, said threshold effective power being that power which would produce either charring or coagulation of surrounding tissue or arcing in the cardiac region;

if desired, varying the high peak power level so that the depth of said lesion varies; and if desired, adjusting the duty cycle to maintain said effective power below said threshold effective power.

21. The method of claim 20 wherein the step of adjusting comprises the further step of adjusting the duty cycle such that the effective power is below a threshold effective power of between approximately 25 watts and approximately 30 watts.

22. The method of claim 20 wherein the step of adjusting comprises the further step of maintaining the duty cycle below approximately 50 percent.

23. The method of claim 20 further comprising the steps of:

measuring the impedance of the cardiac tissue;

comparing the impedance to a predetermined threshold impedance indicative of either charring, coagulation or arcing;

if the impedance is above the threshold level, then reducing said duty cycle; and if the impedance is below the threshold level, then increasing said duty cycle.

24. The method of claim 20 further comprising the steps of:

measuring the temperature of the cardiac tissue;

comparing the temperature to a predetermined threshold temperature indicative of either charring, coagulation or arcing;

if the temperature is above the threshold level, then reducing said duty cycle; and if the temperature is below the threshold level, then increasing said duty cycle.

25. The method of claim 24 further comprising the steps of:

measuring the impedance of the cardiac tissue;

comparing the impedance to a predetermined threshold impedance indicative of either charring, coagulation or arcing;

if the impedance is above the threshold level, then reducing said duty cycle; and if the impedance is below the threshold level, then increasing said duty cycle.

26. In a cardiac tissue ablation procedure using a catheter system having an electrode connected to a power source, said power source producing a power output having alternating instances of high peak power and very low power, said power output having variable power levels and a variable duty cycle for controlling the duration of high peak power and very low power instances, said power source also having a timer for allowing the application of energy to the cardiac tissue for a set time duration, said tissue having, for said set time duration, a threshold power adsorption level above which charring or coagulation of surrounding tissue or arcing in the cardiac region occurs, said catheter system having a maximum peak power capability defined by the structural limitation of the catheter system, a method of producing a deep ablation lesion while maintaining the power absorbed by the tissue below said threshold level comprising the steps of:

setting the high peak power toward the maximum peak power to produce the deep lesion; and setting the duty cycle, based on the high peak power and the set time duration, to maintain the effective power below the threshold power.

27. The method of claim 26 wherein the threshold power is between approximately 25 watts and approximately 30 watts.

28. The method of claim 26 wherein the duty cycle is set below approximately 50 percent.

29. The method of claim 26 wherein the maximum peak power is approximately ninety watts, the time duration is approximately sixty seconds and the duty cycle is approximately 33.3%.

* * * * *